(12) United States Patent
Yaowu

(10) Patent No.: US 6,774,265 B2
(45) Date of Patent: Aug. 10, 2004

(54) BIS-PHOSPHONIUM SALT AND PROCESS FOR PRODUCING THE SAME

(75) Inventor: Sha Yaowu, Beijing (CN)

(73) Assignee: Nippon Chemical Industrial Co., Ltd., Koto-ku (JP)

( * ) Notice: Subject to any disclaimer, the term of this patent is extended or adjusted under 35 U.S.C. 154(b) by 0 days.

(21) Appl. No.: 10/743,728

(22) Filed: Dec. 24, 2003

(65) Prior Publication Data

US 2004/0138504 A1 Jul. 15, 2004

(30) Foreign Application Priority Data

Dec. 27, 2002 (JP) ........................................ 2002-380251

(51) Int. Cl.⁷ .................................................. C07F 9/54
(52) U.S. Cl. ............................................. 568/10; 568/9
(58) Field of Search .................................. 568/8, 9, 10

(56) References Cited

U.S. PATENT DOCUMENTS

| | | | | |
|---|---|---|---|---|
| 2,862,971 A | * | 12/1958 | Thielen et al. ................. | 568/10 |
| 3,364,107 A | * | 1/1968 | Berenson et al. ............ | 514/107 |
| 3,957,978 A | * | 5/1976 | Gastrock et al. ............ | 514/107 |
| 4,620,020 A | * | 10/1986 | Schmidbaur et al. ......... | 556/18 |
| 4,692,504 A | * | 9/1987 | Frank ........................... | 528/89 |

FOREIGN PATENT DOCUMENTS

| | | |
|---|---|---|
| JP | 7-70361 A | 3/1995 |
| JP | 10-114782 A | 5/1998 |
| JP | 10-147590 A | 6/1998 |

OTHER PUBLICATIONS

CA:72:132860 abs of Journal of Pharmacy and Phamacology by Clark et al 22(4) pp 279–283 1970.*

H. Hays, "The Controlled Alkylation of Mono–n–alkylphosphines", Journal of Organic Chemistry, Nov. 1966, pp. 3817–3820, vol. 31.

* cited by examiner

Primary Examiner—Jean F Vollano
(74) Attorney, Agent, or Firm—Smith Patent Office

(57) ABSTRACT

A bis-phosphonium salt represented by the following formula (1) is provided:

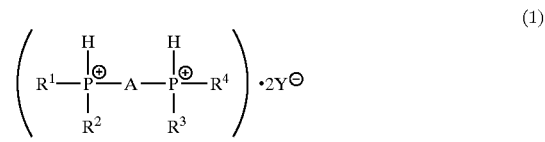

wherein $R^1$, $R^2$, $R^3$, and $R^4$ each represent a linear or branched alkyl group, a cycloalkyl group, an aryl group, or an aralkyl group; A represents an alkylene group; Y represents an anion; $R^1$ and $R^2$ may form a ring; $R^3$ and $R^4$ may form a ring; and $R^1$, $R^2$, $R^3$, and $R^4$ may be the same or different. A process for producing such a bis-phosphonium salt includes a step of allowing a first secondary phosphine and second secondary phosphine to react with a compound in an alcohol solvent selected from a secondary alcohol and tertiary alcohol. The compound is represented by the following formula (5):

$$Y—A—Y \qquad (5)$$

21 Claims, No Drawings

BIS-PHOSPHONIUM SALT AND PROCESS FOR PRODUCING THE SAME

BACKGROUND OF THE INVENTION

1. Field of the Invention

The present invention relates to a new bis-phosphonium salt useful for producing intermediates of various organic phosphorus compounds such as flame retardants and optically active bis-phosphines and also relates to a process for producing the bis-phosphonium salt.

2. Discussion of the Related Art

Organic phosphorus compounds have been widely used for pharmaceuticals, agricultural chemicals, flame retardants, and catalysts for asymmetric synthesis. The bis-phosphonium salt disclosed herein can be converted into various organic phosphorus compounds having two phosphorus atoms according to, for example, the following reaction scheme (I):

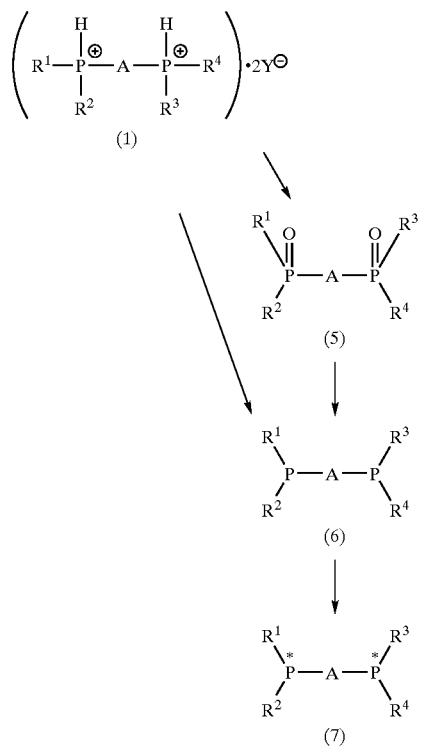

wherein the symbol * represents an asymmetric atom.

For example, phosphine oxide represented by formula (5) in scheme (I) has a high phosphorus content and is therefore useful for flame retardants. The organic phosphorus compound represented by formula (7) in scheme (I) has asymmetric phosphorus atoms and functions as a bis-phosphine ligand having a 1,2-bis(phosphino) ethane skeleton. As is known, bis-phosphine ligands have high asymmetric selectivity and catalytic activity and therefore function as satisfactory catalysts for asymmetric hydrogenation reactions.

As an example of bis-phosphonium salts functioning as antistatic agents, bis-phosphonium bis-sulfonate represented by the following formula (8) is disclosed in pages 1 and 5 of Japanese Unexamined Patent Application Publication No. 7-70361 hereinafter referred to as Patent Document 1):

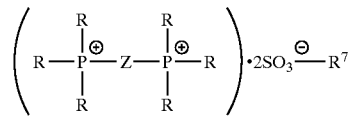

wherein R represents an alkyl group, aryl group, or aralkyl group having 1 to 18 carbon atoms, Z represents an alkylene group having 1 to 6 carbon atoms, and $R^7$ represents an alkyl group having 1 to 40 carbon atoms.

The bis-phosphonium bis-sulfonate is different from the bis-phosphonium salt, represented by formula (1) in scheme (I), according to the present invention.

SUMMARY OF THE INVENTION

It is an object of the present invention to provide a bis-phosphonium salt that is a new compound useful for producing various organic phosphorus compounds and represented by formula (1). It is another object of the present invention to provide a process for producing the bis-phosphonium salt.

A first aspect of the present invention provides a bis-phosphonium salt represented by the following formula (1):

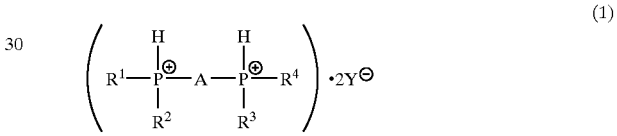

wherein $R^1$, $R^2$, $R^3$, and $R^4$ each represent a linear or branched alkyl group, a cycloalkyl group, an aryl group, or an aralkyl group; A represents an alkylene group; Y represents an anion; $R^1$ and $R^2$ may form a ring; $R^3$ and $R^4$ may form a ring; and $R^1$, $R^2$, $R^3$, and $R^4$ may be the same or different.

A second aspect of the present invention provides a process for producing a bis-phosphonium salt includes a step of allowing a first secondary phosphine and second secondary phosphine to react with a compound in an alcohol solvent selected from a secondary alcohol and tertiary alcohol. The bis-phosphonium salt is represented by the following formula (1):

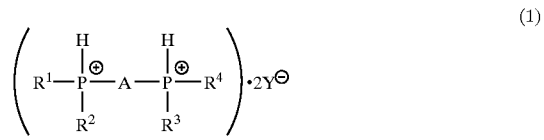

wherein the first secondary phosphine is represented by the following formula (3):

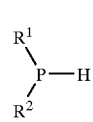

the second secondary phosphine is represented by the following formula (4):

(4)

and the compound is represented by the following formula (5):

(5)

where $R^1$, $R^2$, $R^3$, and $R^4$ each represent a linear or branched alkyl group, a cycloalkyl group, an aryl group, or an aralkyl group; A represents an alkylene group; Y represents an anion; $R^1$ and $R^2$ may form a ring; $R^3$ and $R^4$ may form a ring; and $R^1$, $R^2$, $R^3$, and $R^4$ may be the same or different.

The bis-phosphonium salt represented by formula (1) according to the present invention is a new compound and is useful for producing various phosphorus compounds, particularly flame retardants and bis-phosphonium ligands having a 1,2-bis(phosphino)ethane skeleton.

According to a process of the present invention, the bis-phosphonium salt can be selectively produced at high yield. Such a process is industrially advantageous.

DESCRIPTION OF THE PREFERRED EMBODIMENTS

Embodiments of the present invention will now be described in detail.

A bis-phosphonium salt according to the present invention is represented by the above formula (1). In formula (1), $R^1$, $R^2$, $R^3$, and $R^4$ each represent a linear or branched alkyl group, a cycloalkyl group, an aryl group, or an aralkyl group.

Examples of the alkyl group include a methyl group, an ethyl group, a n-propyl group, a n-butyl group, an i-butyl group, a tert-butyl group, a sec-butyl group, a n-hexyl group, an i-hexyl group, a n-heptyl group, a n-octyl group, an i-octyl group, a n-dodecyl group, an i-dodecyl group, a n-octadecyl group, and an i-octadecyl group, wherein those alkyl groups have 1 to 20 carbon atoms.

Examples of the cycloalkyl group include a cyclopentyl group and a cyclohexyl group.

Examples of the aryl group include a phenyl group, a tolyl group, a xylyl group, and a naphthyl group.

Examples of the aralkyl group include a benzyl group and a phenethyl group.

Those alkyl, aryl, and aralkyl groups may have a substituent, such as a trimethylsilyl group, having no effects on the above reaction. Those alkyl, cycloalkyl, aryl, and aralkyl groups may contain a hetero atom such as an oxygen atom, a sulfur atom, or a nitrogen atom. $R^1$ and $R^2$ may form a ring, and $R^3$ and $R^4$ may also form a ring. $R^1$, $R^2$, $R^3$, and $R^4$ may be the same or different from each other. In the bis-phosphonium salt of the present invention, it is preferable that $R^1$ and $R^4$ be the same, $R^2$ and $R^3$ be the same, $R^1$ and $R^2$ be different from each other, and $R^3$ and $R^4$ be different from each other, because the salt having the above structure can be used for producing optically active bis-phosphines.

In formula (1), A represents an alkylene group, which is preferably a methylene group, an ethylene group, a trimethylene group, a tetramethylene group, a pentamethylene group, an ethylethylene group, a propylene group, a butylene group, a hexylene group, an octylene group, a nonylene group, a decylene group, a dodecylene group, an octadecylene group or the like in particular, wherein those alkylene groups have 1 to 18 carbon atoms. In particular, the alkylene group preferably has 1 to 4 carbon atoms.

In formula (1), Y represents an anion, which may be inorganic or organic. In the present invention, the anion is a halide ion such as a chloride ion, a bromide ion, or an iodide ion; or a sulfonate ion represented by formula (2) described below.

(2)

The bromide ion is particularly preferable.

In formula (2), $R^5$ represents a monovalent organic group, of which examples include a substituted or unsubstituted fluoroalkyl group, a substituted or unsubstituted aryl group, and a substituted or unsubstituted heterocyclic group in particular. Examples of the aryl group include a phenyl group, a p-methylphenyl group, a p-methoxyphenyl group, a p-nitrophenyl group, a p-chlorophenyl group, a pentachlorophenyl group, and a p-fluoromethylphenyl group in particular. Examples of the heterocyclic group include a 2-pyridyl group, a 2-benzothiazolyl group, a 1,3,4-thiadiazole-5-yl group, a 2-methyl-1,3,4-thiadiazole-5-yl group, a 1,2,3,4-tetrazole-5-yl group, a 1-methyl-1,2,3,4-tetrazole-5-yl group, and a 1-phenyl-1,2,3,4-tetrazole-5-yl group.

In the present invention, preferable examples of the bis-phosphonium salt represented by formula (1) include methylene-bis(ethylmethylphosphonium) dibromide, methylene-bis(isopropylmethylphosphonium) dibromide, methylene-bis(n-propylmethylphosphonium) dibromide, methylene-bis(isobutylmethylphosphonium) dibromide, methylene-bis(n-butylmethylphosphonium) dibromide, methylene-bis(tert-butylmethylphosphonium) dibromide, methylene-bis(sec-butylmethylphosphonium) dibromide, methylene-bis(isoheptylphosphonium) dibromide, methylene-bis(n-heptylethylphosphonium) dibromide, methylene-bis(isohexylmethylphosphonium) dibromide, methylene-bis(n-hexylmethylphosphonium) dibromide, methylene-bis(cyclopentylmethylphosphonium) dibromide, methylene-bis(cyclohexylmethylphosphonium) dibromide, methylene-bis(benzylmethylphosphonium) dibromide, methylene-bis(isopropylethylphosphonium) dibromide, methylene-bis(n-propylethylphosphonium) dibromide, methylene-bis(isobutylethylphosphonium) dibromide, methylene-bis(n-butylethylphosphonium) dibromide, methylene-bis(tert-butylethylphosphonium) dibromide, methylene-bis(sec-butylethylphosphonium) dibromide, methylene-bis(isoheptylethylphosphonium) dibromide, methylene-bis(n-heptylethylphosphonium) dibromide, methylene-bis(isohexylethylphosphonium) dibromide, methylene-bis(n-hexylethylphosphonium) dibromide, methylene-bis(cyclopentylethylphosphonium) dibromide, methylene-bis(cyclohexylethylphosphonium) dibromide, methylene-bis(benzylethylphosphonium) dibromide, methylene-bis(isopropyl-n-propylphosphonium) dibromide, methylene-bis(isobutyl-n-propylphosphonium) dibromide, methylene-bis(n-butyl-n-propylphosphonium) dibromide, methylene-bis(tert-butyl-n-propylphosphonium) dibromide, methylene-bis(sec-butyl-n-propylphosphonium) dibromide, methylene-bis(isoheptyl-n-propylphosphonium) dibromide, methylene-bis(n-heptyl-n-propylphosphonium) dibromide, methylene-bis(isohexyl-n-propylphosphonium) dibromide, methylene-bis(n-hexyl-n-propylphosphonium) dibromide, methylene-bis(cyclopentyl-n-propylphosphonium) dibromide, methylene-bis(cyclohexyl-n-propylphosphonium) dibromide, methylene-bis(benzyl-n-propylphosphonium) dibromide, methylene-bis (isobutylisopropylphosphonium) dibromide, methylene-bis(n-butylisopropylphosphonium) dibromide, methylene-bis(tert-butylisopropylphosphonium) dibromide, methylene-bis(sec-butylisopropylphosphonium) dibromide, methylene-bis(isoheptylisopropylphosphonium) dibromide, methylene-bis(n-heptylisopropylphosphonium) dibromide, methylene-bis(isohexylisopropylphosphonium) dibromide, methylene-bis(n-hexylisopropylphosphonium) dibromide, methylene-bis(cyclopentylisopropylphosphonium) dibromide, methylene-bis(cyclohexylisopropylphosphonium) dibromide, methylene-bis(benzylisopropylphosphonium) dibromide, methylene-bis(isobutyl-tert-butylphosphonium) dibromide, methylene-bis(n-butyl-tert-butylphosphonium) dibromide, methylene-bis(sec-butyl-tert-butylphosphonium) dibromide, methylene-bis(benzyl-tert-butylphosphonium) dibromide, methylene-bis(n-tetradecyl-tert-butylphosphonium) dibromide, ethylene-1,2-bis(ethylmethylphosphonium) dibromide, ethylene-1,2-bis(isopropylmethylphosphonium) dibromide, ethylene-1,2-bis(n-propylmethylphosphonium) dibromide, ethylene-1,2-bis(isobutylmethylphosphonium) dibromide, ethylene-1,2-bis(n-butylmethylphosphonium) dibromide, ethylene-1,2-bis(tert-butylmethylphosphonium) dibromide, ethylene-1,2-bis(sec-butylmethylphosphonium) dibromide, ethylene-1,2-bis(isoheptylmethylphosphonium) dibromide, ethylene-1,2-bis(n-heptylmethylphosphonium) dibromide, ethylene-1,2-bis(isohexylmethylphosphonium) dibromide, ethylene-1,2-bis(n-hexylmethylphosphonium) dibromide, ethylene-1,2-bis(cyclopentylmethylphosphonium) dibromide, ethylene-1,2-bis(cyclohexylmethylphosphonium) dibromide, ethylene-1,2-bis(benzylmethylphosphonium) dibromide, ethylene-1,2-bis(isopropylethylphosphonium) dibromide, ethylene-1,2-bis(n-propylethylphosphonium) dibromide, ethylene-1,2-bis(isobutylethylphosphonium) dibromide, ethylene-1,2-bis(n-butylethylphosphonium) dibromide, ethylene-1,2-bis(tert-butylethylphosphonium) dibromide, ethylene-1,2-bis(sec-butylethylphosphonium) dibromide, ethylene-1,2-bis(isoheptylethylphosphonium) dibromide, ethylene-1,2-bis(n-heptylethylphosphonium) dibromide, ethylene-1,2-bis(isohexylethylphosphonium) dibromide, ethylene-1,2-bis(n-hexylethylphosphonium) dibromide, ethylene-1,2-bis(cyclopentylethylphosphonium) dibromide, ethylene-1,2-bis(cyclohexylethylphosphonium) dibromide, ethylene-1,2-bis(benzylethylphosphonium) dibromide, ethylene-1,2-bis(isopropyl-n-propylphosphonium) dibromide, ethylene-1,2-bis(isobutyl-n-propylphosphonium) dibromide, ethylene-1,2-bis(n-butyl-n-propylphosphonium) dibromide, ethylene-1,2-bis(tert-butyl-n-propylphosphonium) dibromide, ethylene-1,2-bis(sec-butyl-n-propylphosphonium) dibromide, ethylene-1,2-bis(isoheptyl-n-propylphosphonium) dibromide, ethylene-1,2-bis(n-heptyl-n-propylphosphonium) dibromide, ethylene-1,2-bis(isohexyl-n-propylphosphonium) dibromide, ethylene-1,2-bis(n-hexyl-n-propylphosphonium) dibromide, ethylene-1,2-bis(cyclopentyl-n-propylphosphonium) dibromide, ethylene-1,2-bis(cyclohexyl-n-propylphosphonium) dibromide, ethylene-1,2-bis(benzyl-n-propylphosphonium) dibromide, ethylene-1,2-bis(isobutylisopropylphosphonium) dibromide, ethylene-1,2-bis(n-butylisopropylphosphonium) dibromide, ethylene-1,2-bis(tert-butylisopropylphosphonium) dibromide, ethylene-1,2-bis(sec-butylisopropylphosphonium) dibromide, ethylene-1,2-bis(isoheptylisopropylphosphonium) dibromide, ethylene-1,2-bis(n-propylisopropylphosphonium) dibromide, ethylene-1,2-bis(isohexylisopropylphosphonium) dibromide, ethylene-1,2-bis(n-hexylisopropylphosphonium) dibromide, ethylene-1,2-bis(cyclopentylisopropylphosphonium) dibromide, ethylene-1,2-bis(cyclohexylisopropylphosphonium) dibromide, ethylene-1,2-bis(benzylisopropylphosphonium) dibromide, ethylene-1,2-bis(isobutyl-tert-butylphosphonium) dibromide, ethylene-1,2-bis(n-butyl-tert-butylphosphonium) dibromide, ethylene-1,2-bis(sec-butyl-tert-butylphosphonium) dibromide, ethylene-1,2-bis(benzyl-tert-butylphosphonium) dibromide, ethylene-1,2-bis(n-tetradecyl-tert-butylphosphonium) dibromide, ethylene-1,2-bis(tert-butylmethylphosphonium)-bis(trifluoromethanesulfonate), ethylene-1,2-bis(sec-butylmethylphosphonium)-bis(trifluoromethanesulfonate), ethylene-1,2-bis(methyl-1,1,3,3-tetramethylbutylphosphonium) dibromide, ethylene-1,2-bis(9-phosphabicyclo[3,3,1]nonane) dibromide, propylene-1,3-bis(tert-butylmethylphosphonium) dibromide, and butylene-1,4-bis(tert-butylmethylphosphonium) dibromide.

A process for producing a bis-phosphonium salt represented by formula (1) according to the present invention will now be described.

The bis-phosphonium salt is produced according to the following reaction scheme (II):

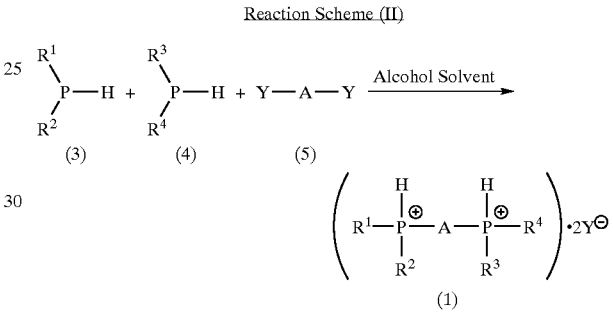

wherein formula (3) represents a first secondary phosphine and formula (4) represents a secondary phosphine. As shown in scheme (II), the first and second secondary phosphines are allowed to react with the compound represented by formula (5) in an alcohol solvent selected from a secondary alcohol and a tertiary alcohol.

$R^1$ to $R^4$ of each secondary phosphine correspond to $R^1$ to $R^4$ of the bis-phosphonium salt, respectively, and represent a linear or branched alkyl group, a cycloalkyl group, an aryl group, or an aralkyl group.

Examples of the alkyl group include a methyl group, an ethyl group, a n-propyl group, a n-butyl group, an i-butyl group, a tert-butyl group, a sec-butyl group, a n-hexyl group, an i-hexyl group, a n-heptyl group, a n-octyl group, an i-octyl group, a n-dodecyl group, an i-dodecyl group, a n-octadecyl group, and an i-octadecyl group, wherein those alkyl groups have 1 to 20 carbon atoms.

Examples of the cycloalkyl group include a cyclopentyl group and a cyclohexyl group.

Examples of the aryl group include a phenyl group, a tolyl group, a xylyl group, and a naphthyl group.

Examples of the aralkyl group include a benzyl group and a phenethyl group.

Those alkyl, aryl, and aralkyl groups may have a substituent, such as a trimethylsilyl group, having no effects on the reaction. Those alkyl, cycloalkyl, aryl, and aralkyl groups may contain a hetero atom such as an oxygen atom, a sulfur atom, or a nitrogen atom. $R^1$ and $R^2$ may form a ring, and $R^3$ and $R^4$ may also form a ring. $R^1$, $R^2$, $R^3$, and $R^4$ may be the same or different from each other.

In the process for producing the bis-phosphonium salt, the first and second secondary phosphines represented by formulas (3) and (4), respectively, are raw materials and may be different from each other or the same. The first and second secondary phosphines are preferably the same because the reaction conditions can be readily controlled. In particular, in the bis-phosphonium salt, it is preferable that $R^1$ and $R^4$ be the same, $R^2$ and $R^3$ be the same, $R^1$ and $R^2$ be different from each other, and $R^3$ and $R^4$ be different from each other, because the salt having the above structure can be used for producing optically active bis-phosphines.

The first and second secondary phosphines can be readily produced according to the following reaction scheme (III) when $R^1$ and $R^2$ do not form a ring, $R^3$ and $R^4$ do not form a ring, and $R^1$ to $R^4$ are each an alkyl group, a cycloalkyl group, an aryl group, or an aralkyl group:

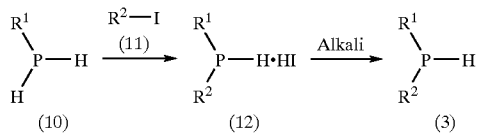

wherein formula (10) represents primary phosphine and formula (11) represents an iodide compound. As shown in scheme (III), the primary phosphine is allowed to react with the iodide compound at 40 to 100° C. in the absence of solvent or in a solvent such as toluene and the reaction mixture is then treated with alkali (see J. Org. Chem., 1966, 31, pp. 3817–3820).

When $R^1$ and $R^2$ form a ring or $R^3$ and $R^4$ form a ring, the first and second secondary phosphines can be produced according to, for example, the following reaction scheme (IV):

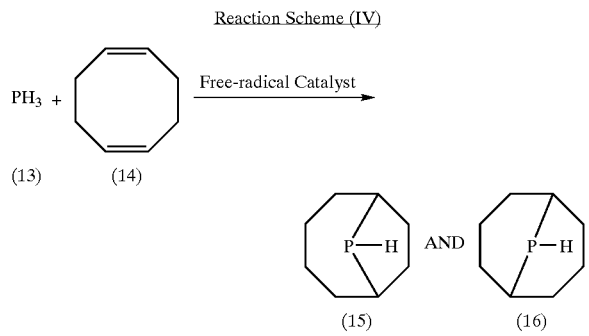

wherein formula (13) represents phosphine, formula (14) represents 1,5-cyclooctadiene, formula (15) represents 9-phosphabicyclo[4,2,1]nonane, and formula (16) represents 9-phosphabicyclo[3,3,1]nonane. As shown in scheme (IV), the phosphine is allowed to react with the 1,5-cyclooctadiene in the presence of a free-radical catalyst, whereby the 9-phosphabicyclo[4,2,1]nonane and 9-phosphabicyclo[3,3,1]nonane are prepared (see Japanese Unexamined Patent Application Publication No. 55-122790). 9-Phosphabicyclo[3,3,1]nonane may be prepared by the following procedure according to needs: 9-phosphabicyclo[4,2,1]nonane and 9-phosphabicyclo[3,3,1]nonane are converted into 9,9-bis(hydroxymethyl)-9-phosphabicyclo[4,2,1]nonane and 9,9-bis(hydroxymethyl)-9-phosphabicyclo[3,3,1]nonane, respectively; alkali is allowed to act on 9,9-bis(hydroxymethyl)-9-phosphabicyclo[4,2,1]nonane and 9,9-bis(hydroxymethyl)-9-phosphabicyclo[3,3,1]nonane, whereby 9,9-bis(hydroxymethyl)-9-phosphabicyclo[3,3,1]nonane is isolated based on a difference in elimination rate of the hydroxymethyl group; and sodium bisulfite is then allowed to act on 9,9-bis(hydroxymethyl)-9-phosphabicyclo[3,3,1]nonane, whereby 9-phosphabicyclo[3,3,1]nonane is isolated.

The compound represented by formula (5) is one of raw materials. Y and A of the compound correspond to Y and A of the bis-phosphonium salt, respectively. A represents an alkylene group, which is preferably a methylene group, an ethylene group, a trimethylene group, a tetramethylene group, a pentamethylene group, an ethylethylene group, a propylene group, a butylene group, a hexylene group, an octylene group, a nonylene group, a decylene group, a dodecylene group, or an octadecylene group in particular, wherein the alkylene group has 1 to 18 carbon atoms. In particular, the alkylene group preferably has 1 to 4 carbon atoms.

Y represents an anion in the bis-phosphonium salt. The anion is introduced to the bis-phosphonium salt by the reaction between the compound represented by formula (5) and the first and second secondary phosphines. Thus, the anion represented by Y is not particular limited as long as the anion has properties fit for the reaction. In the present invention, the anion is preferably a halide ion such as a chloride ion, a bromide ion, or an iodide ion; or the sulfonate ion represented by formula (2). The bromide ion is particularly preferable. $R^5$ in formula (2) represents a monovalent organic group, more specifically a substituted or unsubstituted fluoroalkyl group, a substituted or unsubstituted aryl group, or a substituted or unsubstituted heterocyclic group. Examples of the aryl group include a phenyl group, a p-methylphenyl group, a p-methoxyphenyl group, a p-nitrophenyl group, a p-chlorophenyl group, a pentachlorophenyl group, and a p-fluoromethylphenyl group in particular. Examples of the heterocyclic group include a 2-pyridyl group, a 2-benzothiazolyl group, a 1,3,4-thiadiazole-5-yl group, a 2-methyl-1,3,4-thiadiazole-5-yl group, a 1,2,3,4-tetrazole-5-yl group, a 1-methyl-1,2,3,4-tetrazole-5-yl group, and a 1-phenyl-1,2,3,4-tetrazole-5-yl group.

The molar ratio of the amount of the compound represented by formula (5) to the total amount of the first and second secondary phosphines ranges from 0.02 to 1.0 and preferably 0.4 to 0.6 to increase the product yield and to reduce the loss of the first and second secondary phosphines.

The process for producing the bis-phosphonium salt according to the present invention is characterized in that the first and second secondary phosphines are allowed to react with the compound represented by formula (5) in an alcohol solvent selected from a secondary alcohol and tertiary alcohol. The secondary alcohol and tertiary alcohol that can be used in the above reaction are not particularly limited and any commercially available secondary or tertiary alcohol may be use.

Examples of the secondary alcohol and tertiary alcohol include isopropanol, 2-butanol, 2-pentanol, 3-pentanol, 2-hexanol, 3-hexanol, tert-butanol, tert-pentanol, 1-methylhexanol, and cyclohexanol in particular, wherein those alcohols have an alkyl group with 3 to 12 carbon atoms. The alkyl group may contain a hetero atom such as an oxygen atom. In the present invention, the secondary alcohol and tertiary alcohol preferably each have an alkyl group with 3 to 6 carbon atoms. Tert-butanol is particularly preferable because the product yield is high. Those alcohols may be used alone or in combination.

The molar ratio of the amount of the alcohol solvent to the total amount of the first and second secondary phosphines ranges from 0.1 to 20 and preferably 0.5 to 2.0, because those compounds can be smoothly mixed and the solvent loss can be reduced.

For reaction conditions, the reaction temperature ranges from 20 to 200° C. and preferably 60 to 200° C. This is because the reaction time is extremely long or the reaction does not proceed at a temperature less than 20° C. The reaction time is one hour or more and preferably 6 to 24 hours.

After the reaction, a reaction product is recovered by an ordinary method. The product is washed, recrystallized, and then purified by column chromatography or the like according to needs, whereby the bis-phosphonium salt is obtained.

When Y in formula (1), which represents the bis-phosphonium salt of the present invention, is a halide ion, the halide ion can be replaced with an inorganic or organic acid anion by allowing the bis-phosphonium salt to react with a desired inorganic or organic acid or an alkali metal salt of the acid in a solvent (see Japanese Unexamined Patent Application Publication Nos. 10-147590 and 10-114782).

The bis-phosphonium salt is usually obtained in the form of crystals. This crystalline salt is stable for long term under mild conditions and useful for producing various organic phosphorus compounds.

When $R^1$ and $R^2$ in formula (1) are different from each other and $R^3$ and $R^4$ in formula (1) are different from each other, the bis-phosphonium salt is particularly useful for producing optically active bis-phosphonium ligands having an asymmetric phosphorus atom. When $R^1$, $R^2$, $R^3$, and $R^4$ are the same, the bis-phosphonium salt is useful for producing flame retardants if the salt has high phosphorus content.

EXAMPLES

Examples of the present invention will now be described in detail. The present invention is not limited to these examples.

Example 1

Synthesis of tert-butylmethylphosphine

Over a period of one hour, 780 g (5.5 mol) of methyl iodide was added dropwise into 2,500 ml of a solution containing 450 g (6 mol) of tert-butylphosphine in toluene. The mixture was maintained at 75° C. for 20 hours, whereby white solids were produced in the mixture. The white solids were separated from the mixture by filtration, washed with hexane, and then dried, whereby 948 g of tert-butylmethylphosphonium iodide was prepared.

Subsequently, 14.0 g (60 mmol) of the tert-butylmethylphosphonium iodide and 2.0 g (34.2 mmol) of sodium chloride were fed into a 100-ml two-neck flask from which moisture had been fully removed and of which the atmosphere had been replaced with nitrogen gas. The flask was cooled to 0° C. in an ice bath, and 8.4 ml (120 mmol) of a deaerated 40% NaOH aqueous solution was added dropwise into the flask. Those compounds were mixed for one hour for reaction and the mixture was then kept stationary, thereby obtaining bilayer liquids. The upper liquid was separated, thereby obtaining 5.6 g of transparent, colorless tert-butylmethylphosphine. The product yield was about 90%. The resulting tert-butylmethylphosphine was allowed to react with borane in THF, whereby the tert-butylmethylphosphine was converted into tert-butylmethylphosphine-borane, which was then analyzed.

Identification Data $^1$H NMR (300.4 MHz, CDCl$_3$): σ 0.51 (q, J=97.6 Hz, 3H), 1.22 (d, J=14.9 Hz, 9H), 1.32 (dd, J=10.8 Hz, J=6.1 Hz, 3H), 4.41 (dq, J=355 Hz, J=6.1 Hz, 1H).

$^{31}$P NMR (121.5 MHz, CDCl$_3$): σ 12.3 (d, J=355 Hz).

Example 2

Synthesis of 9-phosphabicyclo[3,3,1]nonane

Into a reactor, 1,843 g (16.69 mol) of 1,5-cyclooctadiene and 3,750 ml of toluene were fed. The atmosphere in the reactor was then fully replaced with nitrogen gas. Subsequently, 731 g (21.50 mol) of phosphine was fed into the reactor, which was then heated to 60° C. Into the reactor, 58.8 g (0.237 mol) of 2,2-azobis(2,4-dimethylvaleronitrile), which functions as a radical initiator, was injected into the reactor with a pressure over a period of three hours. The reactor was then maintained at 60° C. overnight, thereby obtaining a toluene solution containing a mixture of 9-phosphabicyclo[4,2,1]nonane and 9-phosphabicyclo[3,3,1]nonane.

Subsequently, 61.8 g (720 mmol) of 35% formalin and 66.4 g (364 mmol) of 20% hydrochloric acid were added to 136.8 g (306 mmol) of the toluene solution containing 32.2% of the mixture. In the mixture, the ratio of the 9-phosphabicyclo[4,2,1]nonane to the 9-phosphabicyclo[3,3,1]nonane was 6:4. A mixture of the toluene solution, formalin, and hydrochloric acid was allowed to react at room temperature for one hour. A water layer was separated from the resulting mixture, concentrated, and then dried, thereby obtaining 9,9-bis(hydroxymethyl)-9-phosphabicyclo[4,2,1]nonane and 9,9-bis(hydroxymethyl)-9-phosphabicyclo[3,3,1]nonane substantially quantitatively. The 9,9-bis(hydroxymethyl)-9-phosphabicyclo[4,2,1]nonane and 9,9-bis(hydroxymethyl)-9-phosphabicyclo[3,3,1]nonane were dissolved in 120 ml of water, 120 g (120 mmol) of a 4% solution of sodium hydroxide in water was added to the phosphorus compound solution such that the pH of the mixed solution was adjusted to 8.5 or more, and the resulting solution was left for 30 minutes. To the resulting solution, 120 ml of toluene and 22.5 g (282 mmol) of a 50% solution of sodium hydroxide in water were added such that the pH of the liquid mixture was adjusted to 12 or more, and 60 g (580 mmol) of sodium bisulfite was added to the resulting mixture, which was then left for 30 minutes, thereby obtaining a toluene solution containing 9-phosphabicyclo[3,3,1]nonane having a purity of 98%.

Identification Data $^{31}$P NMR (121.5 MHz, CDCl$_3$): σ −53.27 (dt, J=65.6 Hz, J=27.9 Hz),

Example 3

Synthesis of ethylene-bis(tert-butylmethylphosphonium) dibromide

A water-cooled tube was connected to a 50-ml two-neck flask from which moisture had been fully removed and of which the atmosphere had been replaced with nitrogen gas. Into the flask, the following compounds were fed: 0.50 g (6.7 mmol) of deaerated tert-butanol, 0.60 g (5.8 mmol) of tert-butylmethylphosphine, and 0.60 g (3.2 mmol) of 1,2-dibromoethane. The flask was placed in an oil bath and then heated while the compounds were mixed. The mixture was allowed to react at 110° C. for 24 hours. White solids generated in the resulting mixture were separated from the mixture by filtration and then washed with 5 ml of hexane. The resulting solids were dried under vacuum conditions, thereby obtaining 0.84 g of white solid ethylene-bis(tert-butylmethylphosphonium) dibromide. The product yield was 73%.

Identification Data $^1$H NMR (300.4 MHz, CD$_3$OD): σ 1.46 (d, J=18.3 Hz, 18H), 2.11 (d, J=14.1 Hz, 6H), 2.72–3.19 (m, 4H).

$^{31}$P NMR (121.5 MHz, CD$_3$OD): σ 33.7 (br, m).
IR (KBr): 3435, 3363, 2966, 2893, 2363, 2083, 1613, 1475, 1418, 1377, 1317.
Mass (FAB, POS) m/z: 235 (M$^+$–HBr$_2$).

Example 4

Synthesis of propylene-1,3-bis(tert-butylmethylphosphonium) dibromide

A water-cooled tube was connected to a 50-ml two-neck flask from which moisture had been fully removed and of which the atmosphere had been replaced with nitrogen gas. Into the flask, the following compounds were fed: 1.5 g (20 mmol) of deaerated tert-butanol, 1.04 g (10 mmol) of tert-butylmethylphosphine, and 1.11 g (5.5 mmol) of 1,3-dibromopropane. The flask was placed in an oil bath and then heated while the compounds were mixed. The mixture was allowed to react at 90° C. for 24 hours. White solids generated in the resulting mixture were separated from the mixture by filtration and then washed with 5 ml of hexane. The resulting solids were dried under vacuum conditions, thereby obtaining 1.77 g of white solid propylene-1,3-bis (tert-butylmethylphosphonium) dibromide. The product yield was 86%.

Identification Data
$^1$H NMR (300.4 MHz, CD$_3$OD): σ 1.29–1.45 (m, 2H), 1.43 (d, J=18.0 Hz, 18H), 2.03 (d, J=14.5 Hz, 6H), 2.56–2.80 (m, 4H)
$^{31}$P NMR (121.5 MHz, CD$_3$OD): σ 29.8 (br, m).
IR (KBr): 3433, 3376, 2960, 2892, 2369, 2092, 1625, 1470, 1406, 1376, 1319.
Mass (FAB, POS) m/z: 249 (M$^+$–HBr$_2$).

Example 5

Synthesis of ethylene-bis(9-phosphabicyclo[3,3,1]nonane) dibromide

A water-cooled tube was connected to a 25-ml two-neck flask from which moisture had been fully removed and of which the atmosphere had been replaced with nitrogen gas. Into the flask, the following compounds were fed: 2.40 g (32 mmol) of deaerated tert-butanol, 1.19 g (8.4 mmol) of 9-phosphabicyclo[3,3,1]nonane, and 0.96 g (5.1 mmol) of 1,2-dibromoethane. The flask was placed in an oil bath and then heated while the compounds were mixed. The mixture was allowed to react at 100° C. for 18 hours. White solids generated in the resulting mixture were separated from the mixture by filtration and then washed with 5 ml of hexane. The resulting solids were dried under vacuum conditions, thereby obtaining 1.44 g of white solid ethylene-bis(9-phosphabicyclo[3,3,1]nonane) dibromide. The product yield was 72%.

Identification Data
$^1$H NMR (300.4 MHz, D$_2$O): σ 1.58–1.75 (m, 4H), 1.83–2.40 (m, 20H), 2.54–2.74 (m, 4H), 3.04 (t, J=6.9 Hz, 2H), 3.68 (t, J=6.9 Hz, 2H).
$^{31}$P NMR (121.5 MHz, D$_2$O): σ 21.3 (br, m).
IR (KBr): 3420, 3363, 2914, 2859, 2363, 2086, 1628, 1482, 1453, 1408, 1349.
Mass (FAB, POS) m/z: 311 (M$^+$–HBr$_2$).

Example 6

Synthesis of ethylene-bis(tert-butylmethylphosphonium) dibromide

A water-cooled tube was connected to a 50-ml two-neck flask from which moisture had been fully removed and of which the atmosphere had been replaced with nitrogen gas. Into the flask, the following compounds were fed: 1.0 g (7.0 mmol) of deaerated 2-propanol, 0.60 g (5.8 mmol) of tert-butylmethylphosphine, and 0.60 g (3.2 mmol) of 1,2-dibromoethane. The flask was placed in an oil bath and then heated while the compounds were mixed. The mixture was allowed to react at 110° C. for 24 hours. White solids generated in the resulting mixture were separated from the mixture by filtration and then washed with 5 ml of hexane. The resulting solids were dried under vacuum conditions, thereby obtaining 0.75 g of white solid ethylene-bis(tert-butylmethylphosphonium) dibromide. The product yield was 65%.

Identification Data
$^1$H NMR (300.4 MHz, CD$_3$OD): σ 1.46 (d, J=18.3 Hz, 18H), 2.11 (d, J=14.1 Hz, 6H), 2.72–3.19 (m, 4H).
$^{31}$P NMR (121.5 MHz, CD$_3$OD): σ 33.7 (br, m).
IR (KBr): 3435, 3363, 2966, 2893, 2363, 2083, 1613, 1475, 1418, 1377, 1317.
Mass (FAB, POS) m/z: 235 (M$^+$–HBr$_2$).

Comparative Example 1

A water-cooled tube was connected to a 50-ml two-neck flask from which moisture had been fully removed and of which the atmosphere had been replaced with nitrogen gas. Into the flask, the following compounds were fed: 1.0 g (10.8 mmol) of deaerated toluene, 0.60 g (5.8 mmol) of tert-butylmethylphosphine, and 0.60 g (3.2 mmol) of 1,2-dibromoethane. The flask was placed in an oil bath and then heated while the compounds were mixed. The mixture was allowed to react at 120° C. for 12 hours. As a result, a small amount of white solids were generated in the resulting mixture; however, the white solids did not contain a target substance. The resulting mixture was allowed to react with borane in THF, and the reaction mixture was then analyzed. The analysis results showed only borane adducts of the raw materials.

What is claimed is:

1. A bis-phosphonium salt represented by the following formula (1):

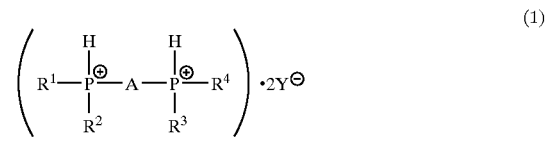

wherein R$^1$, R$^2$, R$^3$, and R$^4$ each represent a linear or branched alkyl group, a cycloalkyl group, an aryl group, or an aralkyl group; A represents an alkylene group; Y represents an anion; R$^1$ and R$^2$ may form a ring; R$^3$ and R$^4$ may form a ring; and R$^1$, R$^2$, R$^3$, and R$^4$ may be the same or different.

2. The bis-phosphonium salt according to claim 1, wherein R$^1$ and R$^4$ are the same, R$^2$ and R$^3$ are the same, R$^1$ and R$^2$ are different from each other, and R$^3$ and R$^4$ are different from each other.

3. The bis-phosphonium salt according to claim 1, wherein the anion is a halide ion or a sulfonate ion represented by the following formula (2):

where R$^5$ represents a monovalent organic group.

4. The bis-phosphonium salt according to claim 3, wherein the anion is a bromide ion.

5. A process for producing a bis-phosphonium salt represented by the following formula (1):

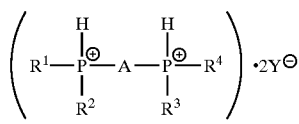
(1)

the process comprising:
a step of allowing a first secondary phosphine and second secondary phosphine to react with a compound in an alcohol solvent selected from a secondary alcohol and tertiary alcohol,
wherein the first secondary phosphine is represented by the following formula (3):

(3)

the second secondary phosphine is represented by the following formula (4):

(4)

and the compound is represented by the following formula (5):

(5)

where R1, R2, R3, and R4 each represent a linear or branched alkyl group, a cycloalkyl group, an aryl group, or an aralkyl group; A represents an alkylene group; Y represents an anion; R1 and R2 may form a ring; R3 and R4 may form a ring; and R1, R2, R3, and R4 may be the same or different.

6. The bis-phosphonium salt according to claim 5, wherein $R^1$ and $R^4$ are the same, $R^2$ and $R^3$ are the same, $R^1$ and $R^2$ are different from each other, and $R^3$ and $R^4$ are different from each other.

7. The process according to claim 5, wherein the anion is a halide ion or a sulfonate ion represented by the following formula (2):

(2)

where $R^5$ represents a monovalent organic group.

8. The process according to claim 7, wherein the anion is a bromide ion.

9. The process according to claim 5, wherein the alcohol solvent is tert-butanol.

10. The process according to claim 5, wherein the first and second secondary phosphines are the same.

11. The bis-phosphonium salt according to claim 2, wherein the anion is a halide ion or a sulfonate ion represented by the following formula (2):

(2)

where $R^5$ represents a monovalent organic group.

12. The bis-phosphonium salt according to claim 11, wherein the anion is a bromide ion.

13. The process according to claim 6, wherein the anion is a halide ion or a sulfonate ion represented by the following formula (2):

(2)

where $R^5$ represents a monovalent organic group.

14. The process according to claim 13, wherein the anion is a bromide ion.

15. The process according to claim 6, wherein the alcohol solvent is tert-butanol.

16. The process according to claim 7, wherein the alcohol solvent is tert-butanol.

17. The process according to claim 8, wherein the alcohol solvent is tert-butanol.

18. The process according to claim 6, wherein the first and second secondary phosphines are the same.

19. The process according to claim 7, wherein the first and second secondary phosphines are the same.

20. The process according to claim 8, wherein the first and second secondary phosphines are the same.

21. The process according to claim 9, wherein the first and second secondary phosphines are the same.

* * * * *